US00PP30261P3

(12) United States Plant Patent
Cain

(10) Patent No.: US PP30,261 P3
(45) Date of Patent: Mar. 5, 2019

(54) SWEET CHERRY TREE NAMED 'IFG CHER-SEVEN'

(50) Latin Name: *Prunus avium*
Varietal Denomination: IFG Cher-seven

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/731,300

(22) Filed: May 22, 2017

(65) Prior Publication Data

US 2018/0338398 P1 Nov. 22, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
See application file for complete search history.

*Primary Examiner* — Keith O. Robinson

(57) ABSTRACT

This invention is a new and distinct sweet cherry tree variety denominated 'IFG Cher-seven'. The new sweet cherry tree is characterized by producing large size dark red fruits having reniform shape and ripening in mid-season. The eating quality remains good after 40 days of cold storage. The fruit stems of 'IFG Cher-seven' remain green, have fresh appearance and have excellent attachment after 40 days of storage.

1 Drawing Sheet

Latin name of the genus and species claimed: *Prunus avium.*

Variety denomination: 'IFG Cher-seven'.

BACKGROUND OF THE INVENTION

The new and distinct sweet cherry tree described and claimed herein originated from open pollinated seeds from a sweet cherry tree designated as 18-19 growing in a commercial orchard located near Delano, in Kern County, Calif. collected in May 2001. The seeds were stratified, germinated and the resulting 59 seedlings were planted in the field near Delano, Kern County, Calif. in April 2002. The present variety of sweet cherry tree was selected as a single plant in May 2005 and was first asexually propagated in January 2006 by grafting onto *Prunus mahalab* rootstock. This propagule was found to reproduce true-to-type by asexual propagation. All propagation was done near Delano, Kern County Calif.

BRIEF SUMMARY OF THE INVENTION

The sweet cherry breeding program has as one of its objectives the development of new sweet cherry varieties that can maintain high quality after long storage and transit times. Sweet cherries shipped internationally may require up to 40 days between harvest and final sale to the end consumer. Few cherry varieties can endure such long storage times and maintain good quality. The present variety is being released because of its improved storage ability and improved fruit quality after long term storage compared to existing sweet cherry varieties.

The new sweet cherry tree 'IFG Cher-seven' is characterized by producing large size dark red fruits having reniform shape. Fruits ripen mid-season, about seven days after the 'Brooks' variety (U.S. Plant Pat. No. 6,676) and approximately with the 'Santina' (Canadian PBR 1202), (not patented in USA) variety. The 'IFG Cher-seven' has firm, medium acid fruit with an excellent cherry flavor. Fruits are more tolerant of rain induced cracking than 'Brooks' or 'Santina'. The tree has a medium-high chilling requirement, somewhat higher than the 'Brooks' variety but somewhat lower than the 'Santina' variety. It appears adapted to regions where 'Santina' can be grown commercially but is not adapted to lower chill climates where the 'Brooks' variety is grown. Fruits of 'IFG Cher-seven' have more desirable darker red skin and flesh than the 'Brooks' variety and exhibits less pitting and stores better than the 'Brooks' and 'Santina' varieties.

In comparison with the 'Santina', the fruit stems 'IFG Cher-seven' remain substantially greener, less shriveled in appearance and have stronger attachment after 40 days of storage. The eating quality is better than 'Santina' after 40 days of cold storage. The fruit shape is reniform compared to the more heart shape of 'Santina'. Fruits of 'IFG Cher-seven' show less tendency to crack on the stylar end as compared to the 'Santina' variety. 'IFG Cher-seven' is self-incompatible having S4S9 pollen alleles as compared to 'Santina', which is self-fertile having the S4 prime gene for self-fertility.

BRIEF DESCRIPTION OF THE DRAWING

The accompanying photographic illustration in FIG. 1 illustrates in full color 'IFG Cher-seven' taken from a 9-year old tree. The photograph was taken outdoors with indirect lighting. The colors are as nearly true as is reasonably possible in a color representation of this type.

An actively growing shoot tip can be seen in the upper portion of the drawing.

Typical mature fruit, fruit in cross section and cleaned and dried fruit pits are displayed in the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification, subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-seven' plants grown in the vicinity of Delano, Kern County, Calif. during 2016, and is believed to apply to plants of the variety grown under similar conditions of soil and climate elsewhere:

Tree:

*General*.—Age — 9 yrs. old. Height — About 3.1 M when pruned. Width — About 3.5 M when pruned. Vigor — Moderately vigorous. Density of foliage — Medium. Form — Spreading. Branching — Medium. Rootstock — *Prunus mahaleb*. Resistance to — Insects: Average typical of *Prunus avium* species. Diseases: Average typical of *Prunus avium* species. Chilling requirements — High: Over 600 hours, similar to 'Santina'. Graft compatibility — Good: produces compatible graft unions with *Prunus avium*, 'Mazzard' seedling (non-patented) and *Prunus mahaleb* seedlings (non-patented).

*Trunk*.—Diameter of 9 year old grafted limb, 20 cm from graft union — About 18.9 cm. Lenticel size — Medium. Lenticel dimensions — Length: About 1.3 cm. Width: About 0.4 cm. Lenticel shape — Elliptical shape oriented horizontally. Lenticel color — Greyed-green: 197C. Trunk surface texture — Rough. Outer bark color — The following colors were observed: Greyed-purple: 187A and Greyed-orange: 166A.

Branches:

1-*year old wood*.—Vertical top growth length — Long: About 90 cm. Horizontal Growth Length — Medium: About 54.8 cm. Diameter — Vertical growth: About 1.1 cm. Horizontal growth: About 2.2 cm. Internode length — About 3.5 cm. Number of lenticels — Few: Approximately 2 lenticels per linear cm. Lenticel size — Small. Lenticel dimensions — Length: About 0.1 cm. Width: About 0.1 cm. Lenticel shape — Round. Bark color — Grey-brown: N199D.

2-*year old wood*.—Length — About 42.5 cm. Diameter — About 1.0 cm. Internode length — About 4.5 cm. Number of lenticels — Few: Approximately 2 lenticels per linear cm. Lenticel dimensions — Length: About 0.3 cm. Width: About 0.1 cm. Lenticel shape — Elliptical shape oriented vertically. Bark color — The following colors were observed: Brown: 200C and N200C.

Buds:

*Vegetative buds*.—Shape — Elongated. Vegetative bud dimensions — Length: About 1.0 cm. Width: About 0.35 cm. Vegetative bud burst — About Feb. 14, 2016.

*Flower buds*.—Flower bud dimensions — Length: About 0.9 cm. Width: About 0.5 cm. Shape — Oval. Placement — At bud positions mostly 1 to 6 on 1-year wood. Average number of flower buds on first year wood: About 5. Number of flower buds per spur on second year wood — 1 to 3. Average: About 2. Color — The following colors were observed: Greyed-orange: 165A and 166B. Flower bud burst — Approximately Feb. 17, 2016.

Leaves:

*Mature leaves*.—Leaf dimensions — Length: About 16 cm. Width: About 7.2 cm. Leaf shape — Ovate: Symmetric on both sides of central axis. Shape of tip — Acuminate: broadly. Shape of base — Attenuate. Margin — Serrated: regular: rounded. Leaf profile — Flat.

*Upper surface*.—Upper surface pubescence — None. Upper leaf surface color — Yellow-green: 147A. Surface texture — Smooth.

*Lower surface*.—Lower surface pubescence — Sparse: all over. Lower leaf surface color — Yellow-green: 147B.

*Petiole*.—Petiole dimensions — Length: About 3.7 cm. Width: About 0.2 cm. Upper surface of petiole color — Greyed-purple: 187A. Lower surface of petiole color — Yellow-green: 147B. Petiole groove — Medium: Approximately 0.8 mm. Petiole pubescence — Sparse: only on upper surface. Venation — Arcuate. Vein color — Yellow-green: 146C.

*Glands*.—Number of glands — 2. Gland dimensions — Length: About 0.27 cm. Width: About 0.2 cm. Gland shape — Globose. Gland location — On petiole. Gland color — Greyed-purple: 185A. Leaf stipule — Not present.

Flowers:

*Blooming period*.—Similar to 'Brooks'.

*Blooming dates*.—First Bloom: Feb. 22, 2016. Full Bloom: Feb. 29, 2016.

*Number of flowers per cluster*.—1 to 3: Average: About 2.

*Corolla*.—Composed of unfused petals, somewhat overlapping.

*Corolla diameter*.—About 3.0 cm.

*Petal number*.—5.

*Petal length*.—About 1.6 cm.

*Petal width*.—About 1.5 cm.

*Margin waviness*.—Medium.

*Division of upper margin*.—Notched.

*Color of petal upper surface*.—The following colors were observed: White: 155D and N155D.

*Color of petal lower surface*.—The following colors were observed: White: 155D and N155D.

*Peduncle*.—Length: About 1.0 cm. Width: About 0.13 cm.

*Peduncle color*.—The following colors were observed: Yellow-green: 144A and 144B.

*Number of sepals*.—5.

*Sepal length*.—About 0.6 cm.

*Sepal width*.—About 0.4 cm.

*Sepal shape*.—Broad ovate.

*Sepal color*.—Upper surface: Yellow-green: 144B. Lower surface: The following colors were observed: Yellow-green: 144A and Greyed red: 181A.

*Filament*.—Length: 0.3 to 1.5 cm. Width: 0.3 mm.

*Filament color*.—White: N155A.

*Anther color*.—Greyed-orange: 163B.

*Pollen color*.—Greyed-yellow: 162A.

*Pollen production*.—Medium.

*Self-compatibility of flowers*.—Self-incompatible.

*Flower compatibility group*.—S4S9.

Fruit:

*General*.—Ripening period — Mid-season: Approximately: May 5, 2016. Use — Fresh market. Keeping quality — Excellent. % Titratable acidity — About 0.83%. Refractometer test — Soluble solids: Brix: About 19.0. Firmtech II (g/mm) — About 277. Flavor — Excellent: Good sugar/acid balance with good cherry flavor. Juice color — Greyed-purple: 187A. Juice amount — Juicy. Eating quality — Excellent.

*Stem*.—Stem — Length: About 3.2 cm. Width: About 0.3 cm. Stem color — Yellow-green: 146B. Stem cavity — Deep. Stem retention during storage — Excellent. Stem storage quality — Excellent.

*Berry*.—Uniformity of size — Slightly variable. Shape — Reniform. Fruit Weight — About 12.1 gm. Apical Diameter — About 2.6 cm. Diameter across suture — About 2.4 cm. Diameter at right angle to suture plane — About 2.9 cm. Suture — None. Percent of excessively deep or split sutures — About 0%. Doubles — About 0%.

*Skin*.—Thickness — Thin to medium. Texture — Smooth, tender. Skin color — Greyed-purple: 187A. Tendency to tip crack — Not susceptible. Tendency to stem cavity crack — Not susceptible. Tendency to suture crack — Somewhat susceptible.

*Flesh*.—Texture — Medium firm. Color — Greyed-purple: 187C. Stone cavity color: Greyed-purple: N186C.

*Stone*.—Shape — Ovate. Length — About 1.2 cm. Width across suture — About 1.0 cm. Width at right angle to suture plane — About 0.74 cm. Type — Semi-free. Surface texture — Slightly rough. Stone Color when dry — Orange-white: 159A. Tendency to split — None. Base — Rounded. Apex — Broadly pointed. Ventral edge — Suture protrudes prominently beyond the horizontal plane of the base of the stone up to the mid-point of the stone. The suture is subtended by 2 narrow ridges converging at the base and apex of the stone. Dorsal edge — Somewhat prominent ridge with slight wing near base, extending from base to apex.

What is claimed:

1. A new and distinct variety of sweet cherry tree as herein illustrated and described.

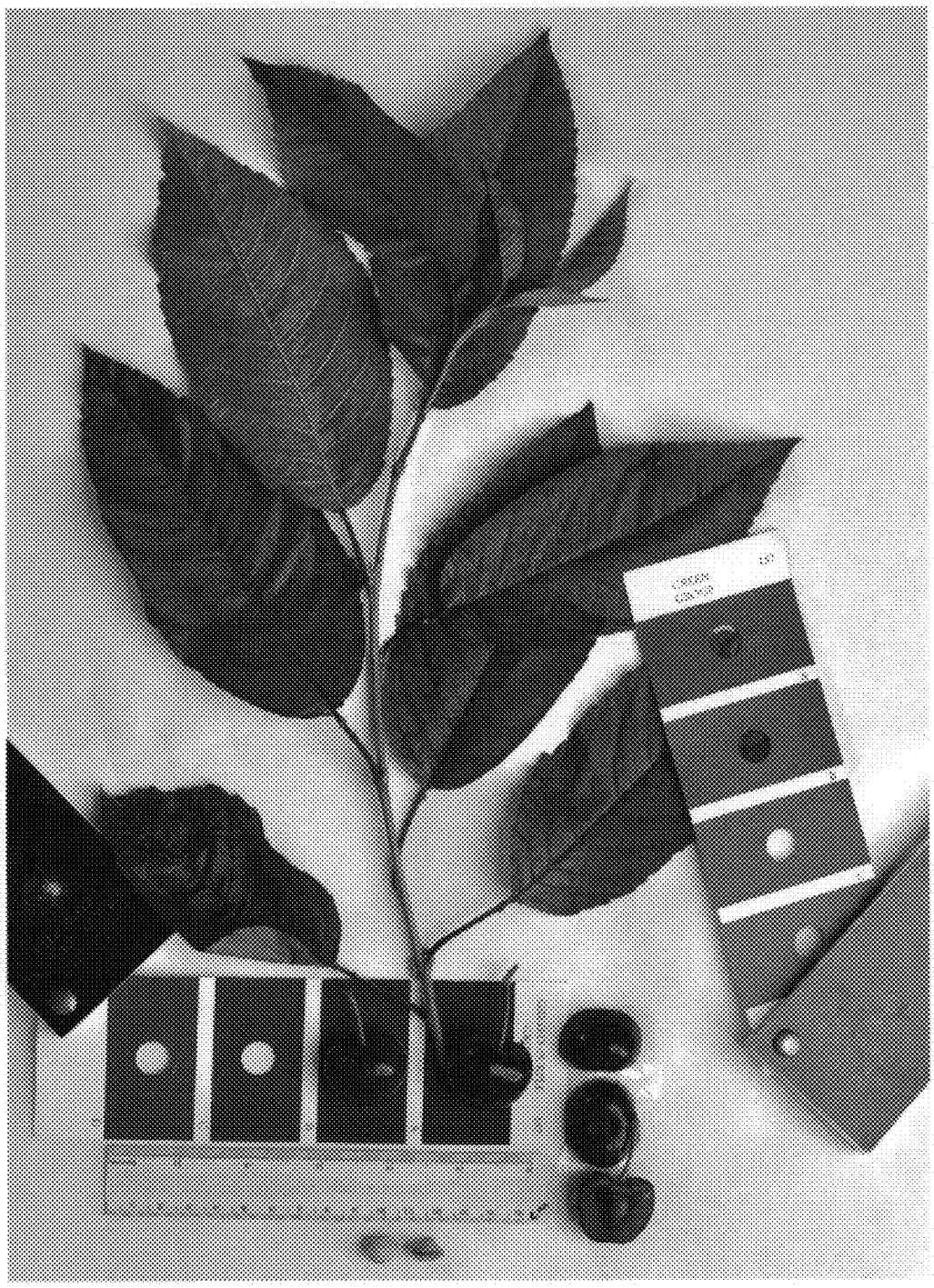

* * * * *